United States Patent [19]

Niederhauser et al.

[11] Patent Number: 5,127,917
[45] Date of Patent: Jul. 7, 1992

[54] PROBE, ESPECIALLY FOR THE RECANALIZATION OF OCCLUSIONS, AND CATHETER ARRANGEMENT WITH SUCH A PROBE

[75] Inventors: Werner Niederhauser, Zurich; Bernhard Meier, Vessy; Urs Bannwart, Bassersdorf, all of Switzerland

[73] Assignee: Schneider (Europe) A.G., Zurich, Switzerland

[21] Appl. No.: 525,413

[22] Filed: May 17, 1990

[30] Foreign Application Priority Data

Jun. 1, 1989 [CH] Switzerland .......... 2056/89

[51] Int. Cl.⁵ .......................... A61M 25/10
[52] U.S. Cl. ........................ 606/191; 606/159; 606/190; 606/194; 604/96; 128/657; 128/772
[58] Field of Search ........ 606/190, 191, 194, 159, 606/192, 129; 128/737, 772, 657; 604/96

[56] References Cited

U.S. PATENT DOCUMENTS

| 3,196,876 | 7/1965 | Miller | 606/191 |
|---|---|---|---|
| 3,433,226 | 3/1969 | Boyd et al. | 128/305 |
| 3,547,103 | 12/1970 | Cook | 128/772 |
| 3,811,446 | 5/1974 | Lerwick et al. | 606/190 |
| 3,999,551 | 12/1976 | Spitz et al. | 606/190 |
| 4,003,369 | 1/1977 | Heilman et al. | 128/772 |
| 4,418,693 | 12/1983 | LeVeen et al. | 606/190 |
| 4,619,274 | 10/1986 | Morrison | 128/772 |
| 4,784,636 | 11/1988 | Rydell | 606/194 X |
| 4,811,743 | 3/1989 | Stevens | 128/772 |
| 4,832,047 | 5/1989 | Sepetka et al. | 128/772 |
| 4,854,325 | 8/1989 | Stevens | 128/657 |
| 4,925,445 | 5/1990 | Sakamoto et al. | 128/772 X |
| 5,026,384 | 6/1991 | Farr et al. | 606/159 |

FOREIGN PATENT DOCUMENTS

| 576753 | 3/1984 | Australia . |
| 145489 | 12/1984 | European Pat. Off. . |
| 259945 | 5/1987 | European Pat. Off. . |
| 279959 | 12/1987 | European Pat. Off. . |
| 316796 | 11/1988 | European Pat. Off. . |
| 2127294 | 9/1983 | United Kingdom . |

OTHER PUBLICATIONS

Mueller "The Surgical Armamentarium" (1980) p. 93.

Primary Examiner—Michael H. Thaler
Attorney, Agent, or Firm—Peter C. Richardson; Lawrence C. Akers; Thomas C. Naber

[57] ABSTRACT

The probe is provided at its distal end with an olive-shaped tip which is solidly joined to a shaft. The shaft is provided with a wire made of stainless steel as well as a spring. The maximum diameter of the tip is preferably approx. 1 mm. The guide catheter is suitable especially for recanalization of coronary and completely obstructed occlusions. The probe is preferably applied together with a baloon catheter itself known.

9 Claims, 3 Drawing Sheets 5,127,917

PROBE, ESPECIALLY FOR THE RECANALIZATION OF OCCLUSIONS, AND CATHETER ARRANGEMENT WITH SUCH A PROBE

BACKGROUND OF THE INVENTION

The invention relates to a probe for the recanalization of vascular occlusions. The invention also relates to a catheter arrangement with such a probe as well as to a catheter arrangement.

The object of the invention is to create a probe of the species mentioned by means of which recanalization, especially of coronary, partly or completely obstructed chronic occlusions, especially of the coronary artery, can be carried out with comparative ease of handling and better prospects for success than hitherto possible.

SUMMARY OF THE INVENTION

Experiments have shown that the probe pursuant to the invention is simple, reliable and cost-effective, especially in combination with a balloon catheter, in itself known. The probe has a higher success rate, presumably as a result of its better penetrability and reduced risk of so-called "subintimal" passage. The probe is especially suitable for chronic occlusions.

The flexible probe introduced into the vessel to be treated is a particularly stable guide for a balloon catheter. An olive-shaped tip, preferably approx. 1 mm wide, at the distal end of the probe reduces unintentional damage to the vessel wall. It has been found that a "high profile" balloon, so called, on a probe pursuant to the invention can be more easily advanced through a narrow stenosis than a so-called "low profile" balloon on a known guide catheter. In all cases studied, it was possible to introduce the balloon catheter on an inserted probe in the final size the first time around, thus obviating the necessity of step-by-step dilatation with different catheters. Use of the catheter pursuant to the invention is also conceivable in nontotal coronary constrictions.

BRIEF DESCRIPTION OF THE DRAWINGS

One embodiment of the invention will now be described in greater detail with reference to FIGS. 1 to 5. In the drawing.

DETAILED DESCRIPTION OF A PREFERRED EMBODIMENT

Figure 1:
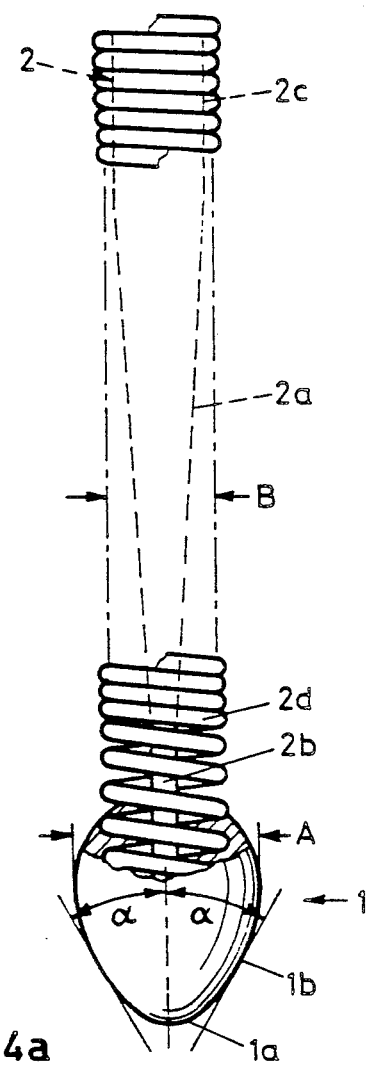
FIG. 1 shows, on a much enlarged scale, a guide catheter pursuant to the invention in partial cross section.

The guide catheter shown in FIG. 1 is provided with a shaft 2 with a partly Teflon-coated wire 2c made of stainless steel. At its distal end wire 2c is conically tapered in one region 2a. At the front end of region 2a steel wire 2c is hammered flat in a region 2b for a length of approx. 2 cm. As a result of the above flat-hammering of steel wire 2 at the distal end, the torsional reliability upon rotation of the catheter is considerably enhanced. Also the danger of fatigue is decreased. The danger of a torsion break of wire 2c at its distal end is thus considerably reduced by the flat-hammering. Experiments have shown, moreover, that this can more or less double the tensile strength of wire 2c. At least in the region 2b shaft 2 is not coated with Teflon.

An olive-shaped tip 1 is firmly secured pull-out-proof to the front end of shaft 2. Tip 1 consists preferably of a silver alloy which is highly visible roentgenographically. The maximum diameter A of tip 1 is preferably approx. 1 mm. The frontal rounded-off end 1a of tip 1 leads to a flank 1b, in which tip 1 exhibits comparatively little convexity. The angle of this rotationally shaped flank 1b to the longitudinal axis of the catheter is approx. about 30° (angle $\alpha$).

The probe is provided with a partly Teflon-coated spring 2d, which preferably consists of a roentgenographically visible material, e.g., tungsten, platinum or gold. Such springs are in themselves known. In order that the probe have good flexibility at its distal end, spring 2d behind tip 1 is uncoated for a length of approx. 3 cm.

Figure 2:
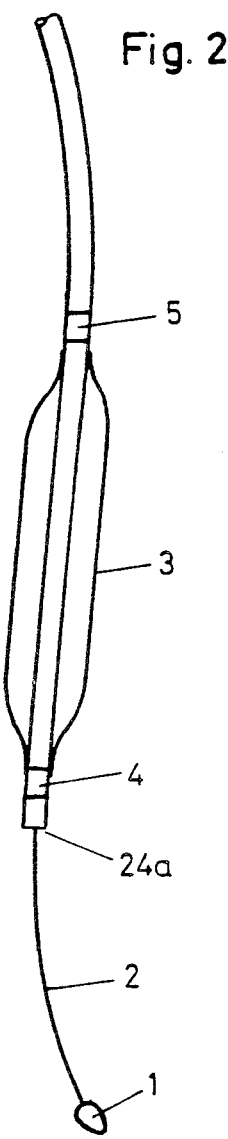
FIG. 2 shows schematically a catheter arrangement with a guide catheter pursuant to the invention.

The catheter arrangement illustrated in FIG. 2 encompasses a probe in accordance with FIG. 1 as well as a ballon catheter 3 with a distal aperture 24a through which the probe is inserted from the front. The probe can be shifted as well as rotated axially at its proximal end by hand. Tip 1 follows these movements. FIGS. 3a to 3f each show a vessel 10 with a lateral branch 10a and an occlusion 11. In accordance with FIGS. 3a and 3b, tip 1 of a probe bent forward at its distal end is advanced to occlusion 11. In accordance with FIG. 3c, balloon 3 of the balloon catheter is now also advanced until the balloon lies directly in front of tip 1 in front of occlusion 11. Because of the balloon catheter, the probe is now additionally stiffened at its distal end, so that tip 1 can now be pushed through occlusion 11 with particular thrust in accordance with FIG. 3d. The closer balloon 3 is to tip 1, the greater the thrust that can be imparted by axial displacement of the probe. Stiffening of the distal end of the tip can thus be easily varied. The suitably placed balloon catheter thus supports the movement of tip 1. In the now at least party recanalized occlusion, the balloon can be introduced into this narrowing in accordance with FIG. 3e. By briefly filling the balloon catheter with liquid under pressure, the occlusion is now made permeable again. As mentioned, this balloon can be of the size suitable to accomplish this. Thanks to tip 1 the movements of the distal end of the probe can be followed roentgenographically by the attending physician particularly well and clearly.

Figure 4A:
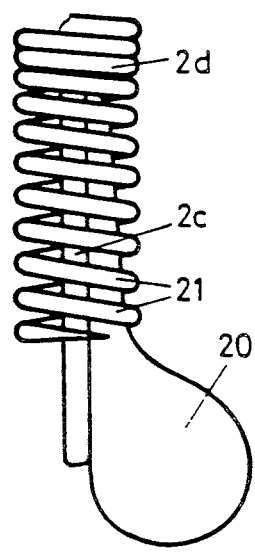
FIGS. 4a and 4b are schematical representations of the distal end of the probe to explain the process for the production of the probe.
Figure 4B:
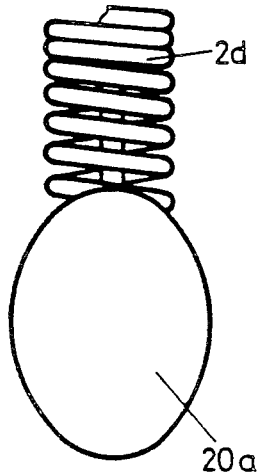

The process pursuant to the invention for the production of a probe will now be elucidated on the basis of FIGS. 4a and 4b. Wire 2c is shoved through spring 2d until its front end projects forward from spring 2d, as shown in FIG. 4a. The frontmost windings 21 of spring 2d are axially lengthened. A silver solder piece 20 is now inserted between spring 2d and wire 2c. The silver solder piece 20 is then heated by a heating current until it melts. As soon as the silver solder piece 20 has fluxed between windings 21 and assumed somewhat the form shown in FIG. 4b, the heating current is removed, whereupon the solder or tip 20a immediately solidifies.

Tip 20a is then ground until it takes the suitable olive-shaped form. The front end of wire 2c as well as the front end of spring 2d are thus firmly joined to tip 1.

Figure 5:
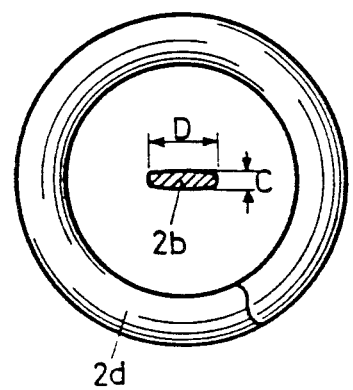
FIG. 5 shows a cross section through the probe in the region in which the wire has been hammered flat.

The front end of wire 2c is preferably hammered flat over a length of preferably approx. 2 cm before tip 1 is applied, so that here wire 2c has approximately the cross section shown in FIG. 5. Dimension D here is preferably approx. 0.12 mm and dimension C preferably approx. 0.03 mm. The diameter of the not yet flat-hammered wire 2c in this region is approx. 0.07 mm. With the exception of the conically tapered region, the diameter of wire 2c remains constant at approx. 0.5 mm. This is also somewhat the diameter of spring 2d.

Figure 3A:
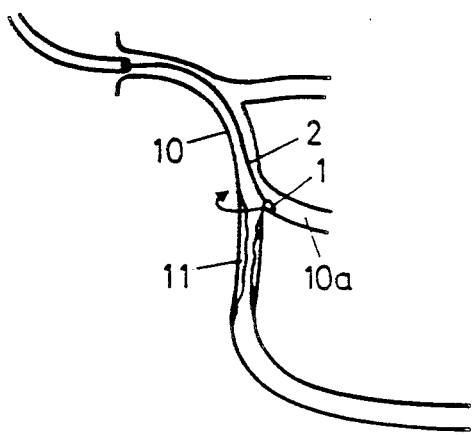
FIGS. 3a to 3f show schematically the individual steps followed in the treatment of an occlusion.
Figure 3B:
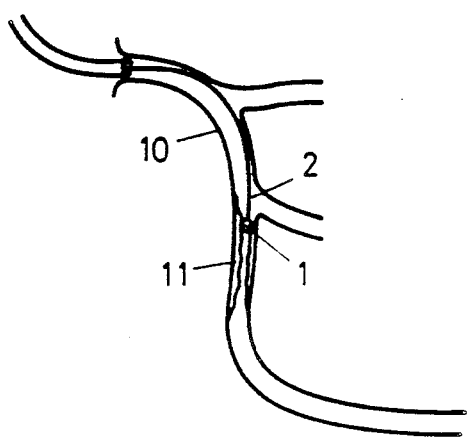
Figure 3C:
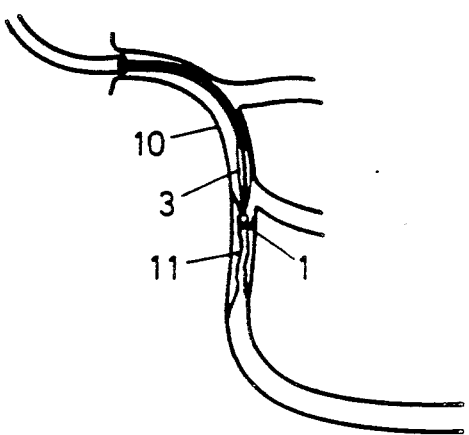
Figure 3D:
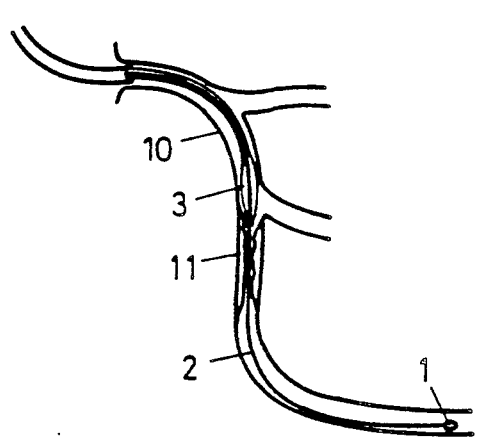
Figure 3E:
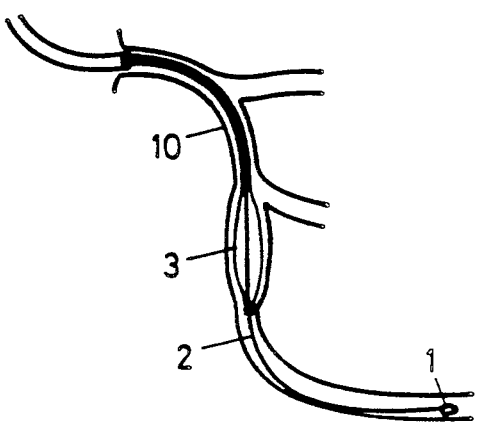
Figure 3F:
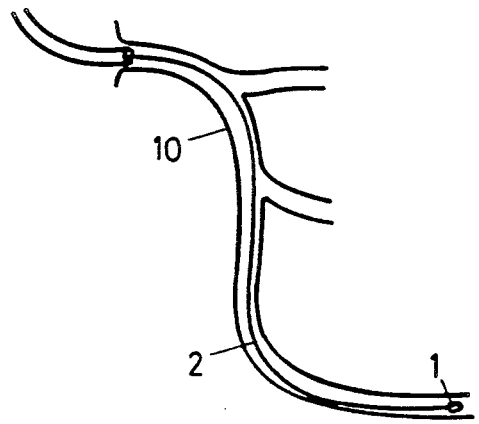

The distal end of the probe can be straight or bent forward. In the latter case, the probe is controllable, i.e., the direction of tip 1 can be changed by one rotation of the probe around its longitudinal axis. In FIG. 3a, such a rotation prevents the probe or tip 1 to enter lateral branch 10a. After tip 1 has formed, the proximal end of spring 2d is soldered with wire 2c. The length of spring 2d is approx. 20-25 cm and the conically tapered region 2a of wire 2c is correspondingly long. Spring other with tip 1.

Figure 6:
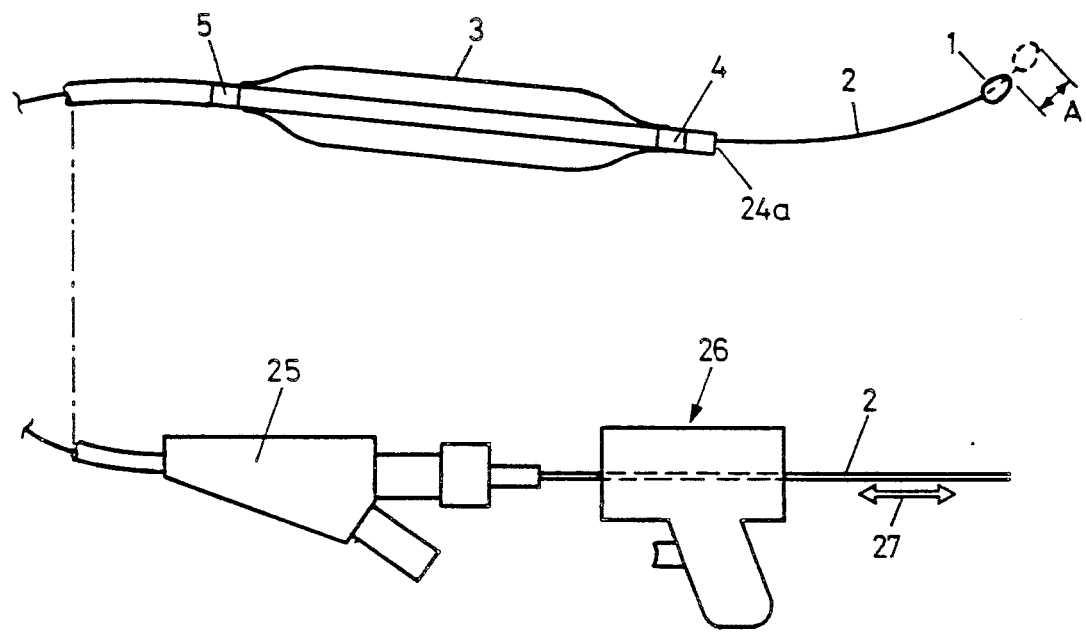
FIG. 6 a diagrammatic view of a catheter arrangement according to a modified embodiment.
Figure 7:
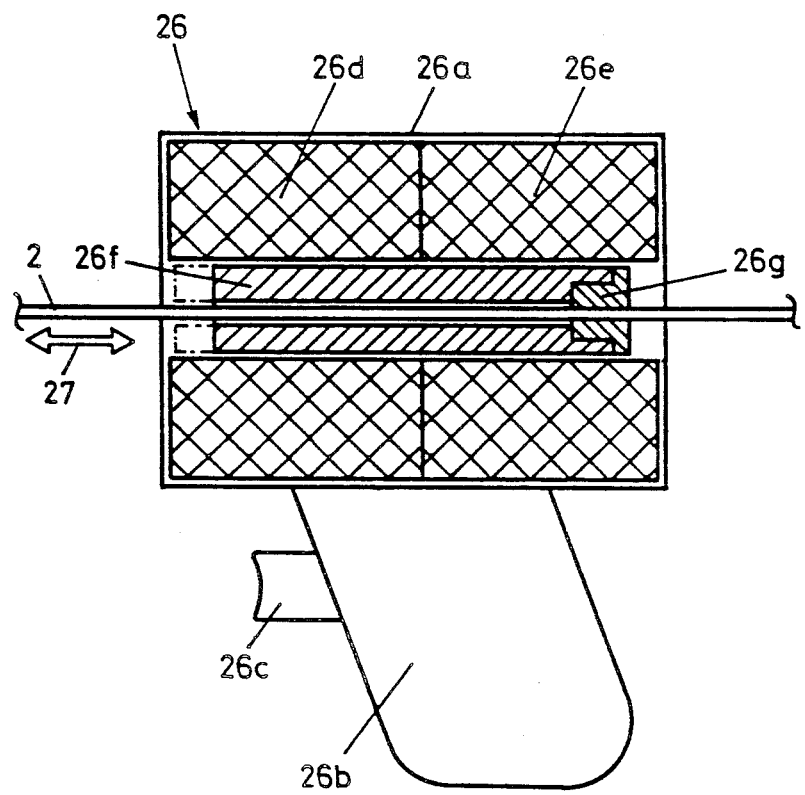
FIG. 7 a side view, partly in section, of a drive incorporated in the embodiment according to FIG. 6.

The modified catheter arrangement according to FIGS. 6 and 7 encompasses a balloon catheter 3 as described above, a well know Y-connector 25 and a drive 26, with which the shaft 2 with the tip 1 can be moved forth and back in the directions of the double arrow 27, in order to better penetrate an occlusion.

The drive 26 has a housing 26a, to which a grip 26b is connected. Inside the housing 26a are two antiparallel magnet coils 26d and 26e. The magnetic field of one of the coils drives an iron core 26f, to which the shaft 2 is fixed with a clamping nut 26g, forth and the field of the other coil drives it back. The shaft 2 can therefore be vibrated in its longitudinal direction with the help of an accumulator and a simple circuit, not shown in the drawings. The frequency of the vibration is in the range of 20-200 Hz. The amplitude at the core 26f is in the range of 2 mm. Due to the damping of the shaft, the amplitude A at the tip 1 is less and in the range of 1 mm. These are the prefered ranges and special cases may need frequences and amplitudes outside these ranges.

To have a exact vibration of the shaft 2, the mass of the coils 26d, 26e and the housing should be much higher than the mass of the core.

We claim:

1. A probe for the recanalization of vascular occlusions, said probe comprising:
    a) a length of wire having a proximal end and distal end section which has in sequence a conically tapered portion and a flat portion;
    b) a spiral spring member which surrounds the distal end section of the length of wire and whose spiral diameter is at least substantially equivalent to the diameter of the length of wire proximal to the conically tapered portion of said distal end section; and
    c) a distal tip attached to the end of the flat portion of said distal end section and to the end of said spring member, said tip having a maximum diameter substantially larger than the maximum spiral diameter of the spring member.

2. A probe as claimed in claim 1 wherein the tip is formed in the shape of an olive, with the more conical end being arranged distally.

3. A probe as claimed in claim 1 wherein the tip has a flank surface axially symmetrical to the length of wire and disposed inwardly at an angle of about 30°.

4. A probe as claimed in claim 1 wherein the tip is retainably bendable laterally.

5. A catheter device for penetrating a vascular occlusion and performing an angioplasty procedure therein, said device comprising a balloon catheter having a distal aperture and a probe whose distal end is disposed distally of the distal aperture of the catheter, said probe comprising:
    a) a length of wire having a proximal end and distal end section which has in sequence a conically tapered portion and a flat portion;
    b) a spiral spring member which surrounds the distal end section of the length of wire and whose spiral diameter is at least substantially equivalent to the diameter of the length of wire proximal to the conically tapered portion of said distal end section; and
    c) a distal tip attached to the end of the flat portion of said distal end section and to the end of said spring member, said tip having a maximum diameter substantially larger than the maximum spiral diameter of the spring member.

6. A catheter device as claimed in claim 5 wherein the tip of the probe is formed in the shape of an olive, with the more conical end being arranged distally.

7. A catheter device as claimed in claim 5 wherein the tip of the probe has a flank surface axially symmetrical to the length of wire thereof and disposed inwardly at an angle of about 30°.

8. A catheter device as claimed in claim 5 wherein the tip of the probe is retainably bendable laterally.

9. A catheter device as claimed in claim 5 wherein the proximal end of the length of wire of the probe is connected to a drive to thereby move the probe back and forth when penetrating a vascular occlusion.

* * * * *